United States Patent [19]
Djafar et al.

[11] Patent Number: 5,047,079
[45] Date of Patent: Sep. 10, 1991

[54] METHOD OF PREPARATION AND USE OF SOLID, PHYTOACTIVE COMPOSITIONS

[75] Inventors: Roger Djafar, Corte Madera; Alan H. Benke, El Cerrito, both of Calif.

[73] Assignee: ICI Americas Inc., Wilmington, Del.

[21] Appl. No.: 233,257

[22] Filed: Jul. 18, 1988

Related U.S. Application Data

[63] Continuation of Ser. No. 897,240, Aug. 18, 1986, abandoned.

[51] Int. Cl.$^5$ .............................. A01N 57/20
[52] U.S. Cl. .................... 71/86; 71/DIG. 1
[58] Field of Search ............... 71/86, DIG. 1

[56] References Cited

U.S. PATENT DOCUMENTS

| | | | |
|---|---|---|---|
| 3,288,846 | 11/1966 | Irani et al. | 260/500 |
| 3,455,675 | 7/1969 | Irani et al. | 71/86 |
| 3,556,762 | 1/1971 | Hamm et al. | 71/86 |
| 3,799,758 | 3/1974 | Franz | 71/86 |
| 3,853,530 | 12/1974 | Franz | 71/76 |
| 3,868,407 | 2/1975 | Franz | 71/86 |
| 3,888,915 | 6/1975 | Alt | 71/86 |
| 3,911,095 | 11/1976 | Gaertner | 71/86 |
| 3,970,695 | 7/1976 | Rueppel | 260/534 R |
| 3,988,142 | 10/1976 | Franz | 71/86 |
| 3,996,040 | 12/1976 | Franz | 71/87 |
| 4,025,331 | 5/1977 | Leber | 71/86 |
| 4,047,927 | 9/1977 | Gaertner et al. | 71/86 |
| 4,062,669 | 12/1977 | Franz | 71/86 |
| 4,082,537 | 4/1978 | Dudkowski | 71/121 |
| 4,084,953 | 4/1978 | Franz | 71/86 |
| 4,119,430 | 10/1978 | Gaertner et al. | 71/86 |
| 4,140,513 | 2/1979 | Prill | 71/86 |
| 4,147,719 | 4/1979 | Franz | 71/86 |
| 4,183,740 | 1/1980 | Jang et al. | 71/92 |
| 4,203,756 | 5/1980 | Gaertner | 71/86 |
| 4,261,727 | 4/1981 | Dutra | 71/86 |
| 4,289,525 | 9/1981 | Pasarela et al. | 71/92 |
| 4,312,662 | 1/1982 | Gaertner | 71/86 |
| 4,315,765 | 2/1982 | Large | 71/86 |
| 4,322,239 | 3/1982 | Dutra et al. | 71/86 |
| 4,397,676 | 8/1983 | Bakel | 71/86 |
| 4,405,531 | 9/1983 | Franz | 544/110 |
| 4,414,158 | 11/1983 | Thummel et al. | 71/86 |
| 4,481,026 | 11/1984 | Prisbylla | 71/86 |
| 4,487,724 | 11/1984 | Felix | 71/86 |
| 4,507,250 | 3/1985 | Bakel | 260/502 F |

FOREIGN PATENT DOCUMENTS 8403607  9/1984  World Int. Prop. O.

*Primary Examiner*—Glennon H. Hollrah
*Assistant Examiner*—Mark W. Russell
*Attorney, Agent, or Firm*—Denis A. Polyn

[57] ABSTRACT

A method for the preparation of a solid, phytoactive composition comprising: (a) reacting an acid form of a phytoactive N-phosphonomethyl-N-carboxylmethyl compound with a liquid amine to form the amine salt of said N-phosphonomethyl-N-carboxylmethyl compound; (b) admixing said salt of said N-phosphonomethyl-N-carboxylmethyl compound with a molten surfactant, the surfactant being solid at ambient temperatures; and (c) cooling said mixture to a temperature below the melting point of the surfactant to form a composition comprising said surfactant and said amine salt of N-phosphonomethyl-N-carboxylmethyl compound interdispersed in the matrix thereof and which is solid at ambient temperatures.

10 Claims, No Drawings

METHOD OF PREPARATION AND USE OF SOLID, PHYTOACTIVE COMPOSITIONS

This is a continuation of application Ser. No. 897,240, filed Aug. 18, 1986 now abandoned.

BACKGROUND OF THE INVENTION

This invention relates to a method for the preparation of novel, solid phytoactive compositions comprising phytoactive compounds containing the moiety:

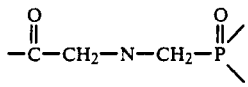

The phytoactive compounds containing the moiety set forth above as Formula I are designated herein as N-phosphonomethyl-N-carboxymethyl compounds or "PMCM" compounds. These compounds and the moiety of Formula I will be further defined and illustrated hereinafter.

THE PRIOR ART

A large number of phytoactive N-phosphonomethyl-N-carboxymethyl compounds are known in the art. The term "phytoactive" as used in describing this invention means effective as a plant growth regulator, as a herbicide, as a defoliant or the like. Illustrative of such N-phosphonomethyl-N-carboxymethyl compounds and their use are: U.S. Pat. Nos. 3,455,675; 3,556,762; 4,405,531; 3,868,407; 4,140,513; 4,315,765; 4,481,026; and 4,397,676, and International Application WO 84/03607.

These patents are illustrative and are incorporated herein by reference. Most of these patents also include descriptions of processes employed to prepare such compounds. The following patents provide additional process descriptions: U.S. Pat. Nos. 3,288,846; 4,507,250, 4,147,719; and 4,487,724. These patents are also incorporated herein by reference.

Certain N-phosphonomethyl-N-carboxymethyl compounds, in particular water soluble N-phosphonomethyl-N-carboxymethyl salts, are often difficult to obtain in a solid form. They can be difficult to crystallize and isolate from aqueous solutions. They can form glassy, non-crystalline solids which transform rapidly into wet cakes when exposed to the air.

Commercial formulations of N-phosphonomethyl-N-dicarboxymethyl compounds are generally not sold in a solid form, but sold as aqueous solutions. These solutions often contain only about 50% N-phosphonomethyl-N-carboxymethyl compound. Consequently, there is substantial waste in terms of storage, transportation charges and container disposal.

N-Phosphonomethyl-N-carboxymethyl compounds in water are usually acidic. They can react with unlined or galvinized steel to produce hydrogen gas which can form a highly combustible gas mixture. If ignited, this mixture can flash or explode, which may cause serious personal injury. Therefore, aqueous solutions of the compounds are usually stored and transported in plastic or specially lined steel containers.

It would be desirable to package and sell N-phosphonomethyl-N-carboxymethyl compounds in a solid form in order to realize substantial savings in terms of storage, transportation and container disposal charges and to avoid the problems associated with N-phosphonomethyl-N-carboxymethyl solutions.

Representative patents generally disclosing so-called wettable or soluble powder compositions containing N-phosphonomethyl-N-carboxymethyl compounds include U.S. Pat. Nos. 4,025,331; 4,414,158; 4,481,026; and 4,405,531. They broadly disclose wettable or powder powder compositions containing a N-phosphonomethyl-N-carboxymethyl compound, an inert solid extender, and one or more surfactants. A disadvantage of such wettable powders is that the solid extender reduces the amount of active ingredients which can be transported in a container of a particular size. A further disadvantage is that many of the phytoactive compounds desirably contained in such powders, particularly N-phosphonomethyl-N-carboxymethyl salts, are hygroscopic or deliquescent. Great care is needed in packaging, storage and use of such wettable/soluble powders. If a final user chooses to employ only a portion of such a powder, extensive precautions must be taken to ensure the stability of the remainder.

A solution to the problem of deliquescence is described in U.S. patent application Ser. No. 762,466 where the active ingredient, a phytoactive N-phosphonomethyl-N-carboxymethyl compound, preferably a salt, is admixed with a solvent and a molten surfactant, the solvent subsequently removed, and the surfactant cooled to a point wherein it becomes solid at ambient temperatures. That product is further processed into particulate form, such as pellets, flakes, granules and the like. The solid composition is subsequently dissolved in a suitable diluent, normally water, at the field site and applied to the plants upon which the compositions' phytoactivity is directed.

Because the acid form of the N-phosphonomethyl-N-carboxymethyl compounds is substantially insoluble in water, or other solvents, the procedure heretofore has been to form these compounds as aqueous salt solutions. The salts are normally formed in situ in an aqueous solvent system. A representative salt is the isopropylamine salt of N-phosphonomethylglycine.

It has now been found, however, that one of the steps in the process described in Ser. No. 762,466 can be eliminated, i.e., the elimination of the preparation of the salt in an aqueous solvent system, and thus a more efficient process obtained, by preparing a water-soluble amine salt of the N-phosphonomethyl-N-carboxymethyl compound by reacting the acid form of the N-phosphonomethyl-N-carboxymethyl compound directly with an amine which is liquid at ambient temperatures. The reaction is continued for a sufficient period of time for the amine to form amine salts of the N-phosphonomethyl-N-carboxymethyl compound, and long enough for the excess amine to evaporate, whereby a solid amine salt of the N-phosphonomethyl-N-carboxymethyl compound is formed. This salt is then admixed with the molten surfactant and solidified in a manner similar to the steps described in Ser. No. 762,466.

SUMMARY OF THE INVENTION

Accordingly, it has now been found that phytoactive N-phosphonomethyl-N-carboxymethyl compositions can be readily prepared in a solid form which is substantially non-hygroscopic and non-deliquescent. The process comprises:

(a) reacting an insoluble acid form of a phytoactive N-phosphonomethyl-N-carboxymethyl compound with an amine which is liquid at ambient temperatures, preferably isopropylamine or butylamine, for a sufficient period of time to form a solid amine salt of said N-phosphonomethyl-N-carboxymethyl compound;

(b) admixing said solid amine salt of said N-phosphonomethyl-N-carboxymethyl compound with a molten surfactant which is solid at ambient temperatures;

(c) cooling said mixture formed in (b) above to a temperature below the melting point of said surfactant to form an N-phosphonomethyl-N-carboxymethyl composition which is solid at ambient temperature; and (d) processing said composition into particulate form, such as pellets, flakes, granules or powders.

As used herein, the term "solid" refers to the physical state wherein the composition has a specific shape and volume and resists deformation. The solid may be processed into any suitable particulate form, such as pellets, flakes, granules, or powder. The solid composition can subsequently be dissolved in a suitable diluent, usually and preferably water, at a remote field site, and applied to the plants upon which the composition's phytoactivity is to be directed.

The N-phosphonomethyl-N-carboxymethyl compounds may be represented by the formula

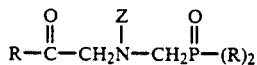

where Z is hydrogen, an organic moiety or an inorganic moiety. Representative patents disclosing N-phosphonomethyl-N-carboxymethyl compounds wherein Z is other than hydrogen include U.S. Pat. Nos. 3,888,915; 3,933,946; 4,062,669; 4,119,430; 4,322,239; and 4,084,953.

In preferred N-phosphonomethyl-N-carboxymethyl compounds, Z is hydrogen or an organic substituent. Representative organic substituents include methylene carboxylic, methylene phosphonic, methylene cyano, carbonyl, such as formyl, acetyl, benzoyl, perfluoroacyl and thiocarbonyl, ethylene, such as cyano, carbamoyl or carboxyl substituted ethylene, and benzene sulfonyl substituents. Representative patents disclosing compounds where the nitrogen contains three organic substituents include U.S. Pat. Nos. 3,455,675; 3,556,762; 4,312,662; 4,261,727; 3,988,142; 3,970,695; 4,180,394; 4,047,927; 3,853,530; 4,203,756; 3,991,095; and 3,996,040. A preferred tertiary nitrogen substituted N-phosphonomethyl-N-carboxymethyl compound is N,N-bis-(phosphonomethyl)glycine. Those N-phosphonomethyl-N-carboxymethyl compounds wherein Z is hydrogen are most preferred when the phytoactivity desired is herbicidal activity.

Representative R's include halogen, —NHOH, —N(R$^1$)$_2$, —OR$^2$, —SR$^2$ and —OH, where R$^1$ is independently selected from hydrogen, alkyl or hydroxyalkyl, preferably containing less than about 5 carbon atoms, alkenyl, preferably containing less than about 5 carbon atoms, or phenyl moieties; R$^2$ is independently selected from hydrogen, alkyl, hydroxyalkyl or chloroalkyl, preferably containing less than about 5 carbon atoms, alkoxy, preferably containing less than about 5 carbon atoms, alkylene amine, preferably containing less than about 12 carbon atoms, phenyl or benzyl moieties.

The phytoactive N-phosphonomethyl-N-carboxymethyl compound used as the starting material in the process of the invention must be capable of reacting with an amine to form a water-soluble amine salt of the phytoactive compound. A preferred phytoactive compound for use in the process and compositions of the invention is N-phosphonomethylglycine. N-Phosphonomethylglycine is an insoluble acid whose preparation is described and claimed in U.S. Pat. No. 3,799,758, Franz.

The amine which is used to react with the acid N-phosphonomethyl-N-carboxymethyl compound can be any organic amine having a carbon chain ranging from about 3 to about 10 carbon atoms in length. The most preferred amine is isopropylamine, however other amines such as n-butylamine, cetylamine, decylamine, and the like can be used. The amine is reacted with the acid N-phosphonomethyl-N-carboxymethyl compound at a mole ratio of about 1:1. An excess of amine can be used; however, it should be reacted with the acid N-phosphonomethyl-N-carboxymethyl compound for a sufficient period of time to allow the excess to evaporate off, leaving a solid composition comprising the amine salt of the N-phosphonomethyl-N-carboxymethyl compound.

The reaction of the amine with the insoluble acid N-phosphonomethyl-N-carboxymethyl compound is normally conducted at ambient temperatures. However, elevated temperatures up to the boiling point of the amine could be used. Whatever amine is used, it must be liquid at ambient temperatures.

The choice of the particular surfactant to be used with a N-phosphonomethyl-N-carboxymethyl compound is important. The choice of a particular surfactant to be used in connection with a a particular N-phosphonomethyl-N-carboxymethyl compound will be easily made by one skilled in the art, without undue experimentation based on the teachings of this application. Whatever surfactant is used, it must be a solid at ambient temperature, i.e., it must have a high melting point. Preferred surfactants have a melting point above 50° C. The surfactant should also not be hygroscopic or deliquescent. When solid, the surfactant should be readily soluble or dispersible in the diluent chosen by the ultimate user of the phytoactive composition. In preferred embodiments, the solid surfactant is soluble in water. The surfactant should cause a minimum amount of foaming, when the final product is subsequently mixed with the diluent.

It is particularly important that the surfactant is solid at ambient temperatures. In practical terms, it must be solid at the highest temperatures to which the solid product may be exposed before it is mixed with the diluent by the ultimate user. Such temperatures are generally in the range of from about −20° to 50° C.

Preferred surfactants for use in the invention are nonionic block copolymers of alkyl oxides having a functional group

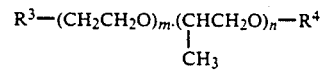

wherein R$^3$ and R$^4$ are the same or different and are selected from hydrogen,

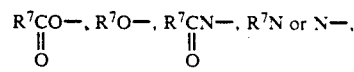

and wherein R$^7$ is selected from an alkylaryl group, wherein the alkyl portion or the alkylaryl group ranges from about eight to about thirty carbon atoms, and mixtures thereof, and wherein m ranges from about 20 to about 200, n ranges from about zero to about ten, and m+n is equal to or greater than about 25.

Examples of R$^7$ include sorbitan; fatty radicals such as coco, oleyl, palmityl, tallow, stearyl, lauryl, soya, castor, nonylphenoxy, dinonylphenoxy, octylphenoxy, and dioctylphenoxy.

Preferred nonionic surfactants for use in the compositions of the invention incude Pluronic surfactants, such as Pluronic F-38, F-68, F-77, F-87, F-88, F-89, F-108 and F-127. The Pluronic surfactants are available commercially (BASF), and comprise ethylene oxide or propylene oxide block copolymers.

The advantages of the use of a nonionic surfactant in the process and compositions of this invention are that they are generally inexpensive, readily available, low or non-irritating, often of low toxicity to mammals and generally, low or non-foaming when under vacuum in a molten state.

Other surfactants can be used, such as cationic, anionic, or amphoteric surfactants. However, they may give rise to foaming. They also may be more toxic to mammals.

Such other surfactants include Emcol (CC-57 (cationic), Arquad C-50 (cationic), Ethomeen 18/12 (cationic), Ethomeen 18/15 (cationic), Ethomeen 18/60 (cationic), Ethomeen T/60 (cationic), Alkaphos K-380 (anionic) and Witconate AOK (anionic).

Mixtures of various nonionic surfactants, or nonionics with cationic, anionic or amphoteric surfactants, can also be used if desired.

The following surfactants, among others, are useful in the processes and compositions of this invention.

TABLE I

| Surfactant | Manufacturer | Structure/Type | m.p. °C. |
|---|---|---|---|
| Trycol 5946 | Emery | tridecyl alcohol EO* | 39 |
| Trycol 5967 | Emery | lauryl alcohol EO | — |
| Trycol 5964 | Emery | lauryl alcohol EO | 39 |
| Trycol 6954 | Emery | nonylphenol 15 EO | — |
| Trycol NP-20 | Emery | nonylphenol 20 EO | 34 |
| Trycol LAL-12 | Emery | lauryl alcohol 12 EO | 32 |
| Trycol LAL-23 | Emery | lauryl alcohol 23 EO | 40 |
| Trycol OAL-23 | Emery | alkyl alcohol 23 EO | 47 |
| Emery 6873 | Emery | — | — |
| Trycol 6988 | Emery | dinonylphenol 15 EO | 55 |
| Pluronic F-88 | BASF | block EO, PO** copolymer | 54 |
| Industrol MS-40 | BASF | polyethylene glycol fatty acid | 48 |
| Iconol DNP-150 | BASF | dinonylphenol 15 EO | 55 |
| Pluronic F-127 | BASF | block EO, PO copolymer | 56 |
| Pluronic F-108 | BASF | block EO, PO copolymer | 57 |
| Plurafac A-39 | BASF | linear alcohol alkoxylate | 56 |
| Alkasurf S-40 | Alkaril | stearic acid ethoxylate, 40 EO | 46 |
| Alkasurf TA-50 | Alkaril | tallow alcohol ethoxylated, 50 EO | 47 |
| Alkasurf OP-40 | Alkaril | octylphenol ethoxylate, 40 EO | 48 |
| Alkasurf LAD-23 | Alkaril | fatty alcohol ethoxylate, 23 EO | 47 |
| Alkatronic PGP 18-8 | Alkaril | block EO, PO copolymer (80% EO) | 52 |
| Alkatronic PGP 23-8 | Alkaril | block EO, PO copolymer (80% EO) | 55 |
| Alkatronic PGP 33-8 | Alkaril | block EO, PO copolymer (80% EO) | 57 |
| T-DET BP-1 | Thompson-Hayward | | 28 |
| T-DET N-100 | Thompson-Hayward | nonylphenol 100 EO | 50 |
| Staley APG 91-3 (solid form) | A. E. Staley | alkyl polyglyoside | |

*EO = ethylene oxide
**PO = ethylene oxide

Additional classes of surfactants which can be used in accordance with the invention are listed in Table II below.

TABLE II

| Surfactants | Type | Structure |
|---|---|---|
| Alkamuls Industrol Alkasurf Trydet | fatty acid ethoxylate | $RCO(CH_2CH_2O)_xCH_2CH_2OH$ |
| Alkamuls Industrol Emerest | di-fatty acid esters | $RCOCH_2CH_2O(CH_2CH_2O)_xCH_2CH_2OCR$ |
| Alkamuls Emsorb | sorbitan ester ethoxylate | $HO(CH_2CH_2O)_w$ ... $(OCH_2CH_2)_xOH$ $CH(OCH_2CH_2)_yOH$ $CH_2(OCH_2CH_2)_zOCR$ |

TABLE II-continued

| Surfactants | Type | Structure |
|---|---|---|
| Alkaminox Trymeen | amine ethoxylate | RN<(CH$_2$CH$_2$O)$_x$CH$_2$CH$_2$OH / (CH$_2$CH$_2$O)$_y$CH$_2$CH$_2$OH |
| Alkasurf Industrol | castor oil ethoxylate | O(CH$_2$CH$_2$O)$_x$CH$_2$CH$_2$OH<br>\|<br>CH$_3$(CH$_2$)$_5$CHCH$_2$CH=CH(CH$_2$)$_7$COCH$_2$<br>      RO—CH<br>      RO—CH$_2$ |
| Pluronic Alkatronic | polyoxypropylene glycol ethoxylate | HO(CH$_2$CH$_2$O)$_x$—(CHCH$_2$O)$_y$—(CH$_2$CH$_2$O)$_z$—H<br>                 \|<br>                 CH$_3$ |
| Alkamidox Emid | alkanolamide ethoxylate | RCN<(CH$_2$CH$_2$O)$_x$H / (CH$_2$CH$_2$O)$_y$H, with O=  |
| Alkasurf Industrol Plurafac Iconol Trycol | alcohol ethoxylate | R—(OCH$_2$CH$_2$)$_x$—OH |

Some surfactants which are solid at ambient temperatures foam. The foaming problem may arise when the final product is subsequently mixed with a diluent by the ultimate user. Therefore, some embodiments of the invention include an anti-foaming agent. The anti-foaming agent may be added any time prior to solidification of the molten surfactant.

Representative of useful anti-foaming agents include compounds such as Silcolapse 5008 (silicone-based antifoam) and Anti-foam Emulsion Q-94 (SWS Silicones Corp.).

In addition to the N-phosphonomethyl-N-carboxymethyl compound, the surfactant and the anti-foaming agent, the composition can also include other conventional adjuvants such as drying aids, heat stabilizers, ultraviolet absorbers, dispersants, wetting agents, and other agriculturally acceptable materials. Representative drying aids include Microcel E, Aerosil 200 and Hi-Sil® 233. Representative ultraviolet absorbers include Tinuvin 770, Tinuvin P, and dinitroanilines.

The ratio of N-phosphonomethyl-N-carboxymethyl compound to surfactant varies over a wide range. Since it known that the choice of a particular surfactant can affect the phytoactivity of the N-phosphonomethyl-N-carboxymethyl compounds used in accordance with this invention, the desired activity of the solid composition should be considered when selecting a particular surfactant. As much surfactant as desired may be employed so long as the products dissolve totally or disperse readily in the diluent prior to application. For cost considerations, a minimum of surfactant should be used which still enables the objects of the invention to be obtained, e.g., the production of a solid product which is substantially non-hygroscopic. The ratio of N-phosphonomethyl-N-carboxymethyl compound to surfactants by weight, is typically from about 10:1 to about 1:10. The preferred ratio is from about 4:1 to about 1:2. The most preferred ratio is from about 2:1 to about 1:1.

Representative formulations of the compositions of this invention are as follows. The formulations are based on percent by weight, unless otherwise noted.

| | |
|---|---|
| 69.3% | isopropylamine salt of N-phosphonomethylglycine |
| 30.7% | Tetronic 980 (m.p. 58° C.) |
| 100.0% | Total |
| 69.3% | isopropylamine salt of N-phosphonomethylglycine |
| 30.7% | F-108 (m.p. 57° C.) |
| 100.0% | Total |
| 69.3% | butylamine salt of N-phosphonomethylglycine |
| 30.7% | Tetronic 909 (m.p. 59° C.) |
| 100.0% | Total |
| 69.3% | cetylamine salt of N-phosphonomethylglycine |
| 30.7% | Pluronic f-108 (m.p. 57° C.) |
| 100.0% | Total |

The solid compositions in accordance with this invention are characterized in that the N-phosphonomethyl-N-carboxymethyl compound forms an intimate mixture with the surfactant. The N-phosphonomethyl-N-carboxymethyl compound is initially dispersed throughout a surfactant matrix. It is believed that such an intimate dispersion prevents absorption of moisture by the N-phosphonomethyl-N-carboxymethyl compounds.

The compositions of this invention can be prepared in any suitable manner. A preferred process, however, is as follows.

First, a quantity of an acid N-phosphonomethyl-N-carboxymethyl compound is obtained. It normally will be granular or powdered in form. This compound is then reacted or admixed preferably at ambient temperatures with the liquid amine, preferably isopropylamine, in a mole ratio of approximately 1:1 such that the amine salt of the N-phosphonomethyl-N-carboxymethyl compound is formed. This amine salt is also a solid and conventionally in granular or powder form. Next, the newly formed amine salt of the N-phosphonomethyl-N-carboxymethyl compound is admixed with the molten surfactant for a sufficient period of time to obtain complete dispersal of the N-phosphonomethyl-N-carboxymethyl granules or powder within the matrix of the surfactant.

Preferably, the surfactant is added in the molten state, although in some embodiments it is initially merely admixed with the N-phosphonomethyl-N-carboxymethyl compound and the temperature then raised above the melting point of the surfactant. Initial use of a molten surfactant permits easy mixing.

In order to form or maintain the molten surfactant, the lower limit on the temperature of the initial mixture is the melting point of the surfactant. The upper limit is the temperature at which a particular N-phosphonomethyl-N-carboxymethyl compound, surfactant or other additives will decompose. When isopropylamine salts of N-phosphonomethylglycines are chosen as a N-phosphonomethyl-N-carboxymethyl compound, temperatures in the range of 50° to 80° C. are generally employed.

As the surfactant cools a viscous final mixture is formed. Upon cooling, the final mixture readily solidifies.

The resulting solid composition can then be processed into any suitable particulate form, such as pellets, flakes, granules, or powder, by conventional techniques. As will be readily appreciated by one skilled in the art, the size of the final particle will effect the ease of solution or dispersion of the final product in the diluent by the ultimate user. Generally, the ease of solution or dispersion increases as particle size decreases. In contrast, however, the ease of handling the final product increases as particle size increases. The more soluble or dispersible the solid composition, the larger the particle size than can be employed. In preferred embodiments, the final product is processed into particles ranging from powders having a diameter of about 3 to about 15 microns, to granules having a diameter of about 8 to about 30 mesh to flakes.

The following examples illustrate production of the compositions of the invention in accordance with the process described herein. All percentages are based on weight, unless otherwise clearly indicated.

EXAMPLE 1

In a laboratory rotary evaporator, 12.5 g of Tetronic ® 908 surfactant (block copolymer of ethylene oxide and propylene oxide from BASF), m.p. 58° C., is melted in a 200 milliliter (ml) round-bottom flask at 70° C. To the molten surfactant 42.5 g of the isopropylamine salt of N-phosphonomethylglycine at ambient temperature is added slowly while the elevated temperature is maintained. The mixture is then solidified by cooling to room temperature. The solids obtained are removed from the flask with a spatula and ground into a powder with a pestle and a mortar under nitrogen. A sample of the powder left in an open crucible did not deliquesce.

EXAMPLE 2

A composition is prepared as in Example 1, except for using 12.5 g of Igepal DM 970 (dialkylphenoxypoly(ethyleneoxy)ethanol from GAF Corp.) as the surfactant. A solid is obtained which does not deliquesce upon standing in the open.

EXAMPLE 3

A composition is prepared as in Example 1, except for using 15 g of Iconol DNP 150, m.p. 55° C., as the surfactant, 1 g of Hi-Sil ® (fumed silica from PPG), 2 drops of anti-foaming agent (Silcolapse 5008) and evaporating at 100° C. for one-half hour at 1 mm Hg (absolute). A solid is obtained which does not deliquesce upon standing in the open.

EXAMPLE 4

A composition is prepared as in Example 1, except for using 15 g of Pluronic ® F-108, m.p. 56° C., as the surfactant. The viscous paste obtained is solidified by cooling to room temperature. It does not deliquesce upon standing in the open.

EXAMPLE 5

A composition is prepared as in Example 4, except for using a mixture of 2 surfactants (10 g of Pluronic ® 17R8 and 5 g of Trycol ® 5946, ethoxylated alkylphenol surfactant from Emery). The viscous paste obtained solidifies after cooling to room temperature. It does not deliquesce upon standing in the open.

EXAMPLE 6

A composition is prepared as in Example 1, except for using 15 g of Pluronic ® F-108, m.p. 56° C., 1 g of Hi-Sil ® (fumed silica from PPG). The product obtained solidifies quickly when cooled. It does not deliquesce upon standing in the open.

EXAMPLE 7

A composition is prepared as in Example 1, except for using 25 g of Plurafac A-39 (a linear alcohol ethoxylate surfactant from BASF), m.p. 56° C., as the surfactant. The viscous liquid obtained solidifies when cooled to room temperature. It does not deliquesce upon standing in the open.

The phytoactive compositions of this invention are effective when subsequently dissolved or dispersed in a suitable diluent, preferably water, and applied to the locus desired by spray or other conventional means. Conventional adjuvants, including wetting agents, penetrating agents, spreading or sticking agents, such as dispersing agents can be added to the final solution or dispersion.

The amount of the composition which constitutes a phytoactive amount depends on the nature of the plants and the effect desired. The rate of application generally varies from about 0.01 to about 50 pounds of N-phosphonomethyl-N-carboxymethyl compound per acre, preferably about 0.1 to about 25 pounds per acre with the actual amount depending on the overall cost and the desired results. It will be readily apparent to one skilled in the art that compositions exhibiting lower phytoactivity will require a higher application rate than the more active compounds for the same degree of effectiveness.

What is claimed is:
1. A method for the preparation of a solid, substantially non-hygroscopic and non-deliquescent phytoactive composition comprising:
   (a) admixing an amine salt of a N-phosphonomethyl-N-carboxylmethyl compound with a molten surfactant, the lower limit on the temperature of the mixture being the melting point of said surfactant and the upper limit being the temperature at which said amine salt of said N-phosphonomethyl-N-carboxylmethyl compound will decompose, the surfactant being solid at ambient temperatures wherein the ratio of N-phosphonomethyl-N-carboxylmethyl compound to surfactant, by weight, is from about 10:1 to about 1:10; and (b) cooling said mixture to a temperature below the melting point of the surfactant to form a composition comprising said surfactant and said amine salt of N-phosphonomethyl-N-carboxylmethyl compound interdispersed in the matrix thereof and which is solid at ambient temperatures.

2. The method in accordance with claim 1 wherein said amine salt is the isopropylamine salt.

3. The method in accordance with claim 1 wherein said N-phosphonomethyl-N-carboxylmethyl compound is N-phosphonomethylglycine.

4. The method in accordance with claim 1 wherein said N-phosphonomethyl-N-carboxylmethyl compound is N,N-bis-(phosphonomethyl)glycine.

5. The method in accordance with claim 1 further comprising processing the solid, phytoactive composition into a particulate form.

6. The method in any of claims 1 through 5 wherein the surfactant is nonionic.

7. The method in any of claims 1 through 5 wherein the surfactant is an ethylene oxide or propylene oxide block copolymer.

8. The method in any of claims 1 through 5 wherein the surfactant is a block copolymer of alkyl oxides having a functional group

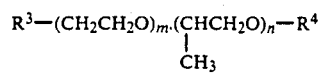

wherein R and R' are independently selected from hydrogen,

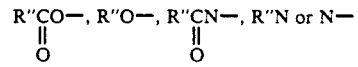

wherein R" is selected from an alkyl group having from about 8 to about 30 carbon atoms or alkylaryl groups, wherein the alkyl portion of the alkylaryl group ranges from about 8 to about 30 carbon atoms, and mixtures thereof, and wherein m ranges from about 20 to about ab 200, n ranges from about 0 to about 10, and m+n is equal to or greater than about 25.

9. The method of claim 1 which includes the additional step of processing said composition into particulate form, such as pellets, flakes, granules, or powders.

10. The method in accordance with claim 2 wherein the temperature of said melt is in the range of 50° to 80° C.

* * * * *